United States Patent [19]

Minn

[11] 4,283,338

[45] Aug. 11, 1981

[54] PROCESS FOR PRODUCING O,O-DIALKYL DITHIOPHOSPHORIC ACID ESTERS

[75] Inventor: James Minn, Hattiesburg, Miss.

[73] Assignee: Boots Hercules Agrochemicals Co., Wilmington, Del.

[21] Appl. No.: 123,548

[22] Filed: Feb. 22, 1980

[51] Int. Cl.$^3$ .................... C07D 209/48; C07F 9/173; C07D 319/12
[52] U.S. Cl. ............................ 260/326 E; 260/340.6; 260/340.9 R; 260/979; 549/14; 549/21
[58] Field of Search ............... 260/326 E, 979, 340.6, 260/340.9; 549/14, 21

[56] References Cited

U.S. PATENT DOCUMENTS

| | | | |
|---|---|---|---|
| 2,725,328 | 11/1955 | Diveley et al. | 260/340.6 |
| 2,815,350 | 12/1957 | Speck | 260/979 |
| 3,849,439 | 11/1974 | Imamura et al. | 260/326 E |

*Primary Examiner*—Donald G. Daus
*Assistant Examiner*—M. C. Eakin
*Attorney, Agent, or Firm*—Hazel L. Deming

[57] ABSTRACT

Disclosed is a method for improving the yield of dialkyl dithiophosphoric acid esters produced by the Lewis acid catalyzed reaction of an O,O-dialkyl dithiophosphoric acid and an organic chloride. More specifically, the method concerns the improvement wherein the reaction is conducted under sufficient pressure to maintain the liberated hydrogen chloride in the reaction system during the course of the reaction.

6 Claims, No Drawings

PROCESS FOR PRODUCING O,O-DIALKYL DITHIOPHOSPHORIC ACID ESTERS

This invention relates to an improved process for the preparation of dialkyl dithiophosphoric acid esters and more specifically relates to a method for improving the yield of dialkyl dithiophosphoric acid esters produced by the Lewis acid catalyzed reaction of an O,O-dialkyl dithiophosphoric acid and an organic chloride.

It is known from U.S. Pat. No. 2,815,350 to Speck that the rate of reaction between O,O-dialkyl dithiophosphoric acids and chloro- organic compounds wherein a chlorine is replaced by an O,O-dialkyl dithiophosphoric acid can be greatly accelerated by carrying out the reaction in the presence of a catalytic amount of a Lewis acid such as the chloride of zinc, iron or tin and removing the hydrogen chloride by-product as it is formed. Moreover, Diveley and Lohr in U.S. Pat. No. 2,725,328 teach carrying out the uncatalyzed reaction of an O,O-dialkyl dithiophosphoric acid with a 2,3-dihalo-p-dioxane in the presence of a sequestering agent such as an amine or inorganic base which combines with the liberated hydrogen halide as formed. On an industrial scale, the use of sequestering agents is not practical from an economic standpoint and the usual practice involves passing a slow current of inert gas through the mixture to carry off the liberated hydrogen halide to a scrubber wherein it is recovered by neutralization with a base such as lime.

Now in accordance with the present invention it has been found that not only is it unnecessary to remove or sequester the hydrogen chloride liberated by the reaction of an O,O-dialkyl dithiophosphoric acid and an organic chloride in the presence of a metal chloride catalyst but that the retention of hydrogen chloride in the reaction system by conducting the reaction under pressure leads to substantial improvement in the yield of ester product.

The process of this invention is more particularly set forth in the following examples in which all parts and percentages are by weight.

EXAMPLE 1

A closed reaction vessel equipped with heating means, agitator, thermometer, addition port and condenser means was charged with 0.3 mole of O,O-diethyl dithiophosphoric acid as a 46% solution in cyclohexane and 0.0022 gram atom of zinc dust. Heating and agitation were commenced and when the temperature of the charge reached 80° C., 0.13 mole of 2,3-dichloro-p-dioxane was added gradually over a 1 hour period. The reaction mixture was agitated at 80°–85° C. for an additional 3 hour period during which time the pressure increased to about 15 p.s.i.g. The reaction mixture was cooled to 25° C., and the product was recovered by washing the cooled mixture with brine and then dilute alkali, and then distilling the solution to remove the cyclohexane. The isolated product amounted to 57.5 grams (95.0% yield based on the 2,3-dichloro-p-dioxane) and contained 82.4% of the cis and trans isomers of bis(diethyl dithiophosphate) of p-dioxane-2,3-dithiol, as determined by high pressure liquid chromatography.

For the sake of comparison the above procedure was repeated with the exception that the reaction was carried out in a vessel open to the atmosphere and the hydrogen chloride by-product was vented to the atmosphere. The isolated product amounted to 53.5 grams (yield of 88.3%) and contained 89.7% of the cis and trans isomers of the bis(diethyldithiophosphate) of p-dioxane-2,3-dithiol.

EXAMPLES 2-5

The general procedure of Example 1 was followed except that: the closed reaction vessel was charged with 0.11 mole of O,O-diethyl dithiophosphoric acid as a 60% solution in benzene and 0.005 gram atom of zinc dust; 0.10 mole of N(1,2-dichloroethyl) phthalimide as a 50% solution in benzene was added gradually over a 1 hour period; the reaction mixture was agitated at 85° C. for an additional 8 hour period; and the pressure in the vessel increased to 10 to 15 p.s.i.g.

Details of these examples and controls therefor wherein each reaction was repeated using the comparison procedure set forth in Example 1 are tabulated below:

| Ex. No. | Pressure (p.s.i.g.) | Product Grams | Yield (%) | Purity (%)* |
|---|---|---|---|---|
| 2 | 10–15 | 27.8 | 70.6 | 80.4 |
| Control | — | 26.5 | 67.3 | 80.6 |
| 3 | 10–15 | 27.8 | 70.6 | 82.7 |
| Control | — | 26.5 | 67.3 | 81.5 |
| 4 | 10–15 | 28.6 | 72.6 | 80.2 |
| Control | — | 24.2 | 61.4 | 80.8 |
| 5 | 10–15 | 27.2 | 69.0 | 76.6 |
| Control | — | 25.8 | 65.5 | 80.5 |

*Percentage of cis and trans isomers in isolated product

As stated, the invention relates to an improved process for effecting the reaction defined by the equation

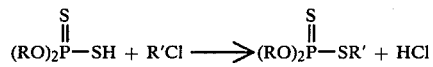

where R is an alkyl group and R'Cl is an organic chloride and wherein the reaction is effected in the presence of a catalytic amount of zinc chloride, ferrous chloride or stannous chloride and in the absence of a sequestering agent for the hydrogen chloride liberated by the reaction, the improvement comprising conducting the reaction under sufficient pressure to maintain the liberated hydrogen chloride in the system during the course of the reaction.

The process of this invention is applicable to any O,O-dialkyl dithiophosphoric acid and is particularly interesting where the alkyl groups are those having 1 to 4 carbon atoms because of the utility of the resulting products as insecticides. However, there is no criticality with respect to the present process insofar as the alkyl groups themselves are concerned and the invention is not limited with respect thereto.

All chloro-organic compounds which contain at least one chlorine which is sufficiently active to be replaced by the O,O-dialkyl dithiophosphoric acid radical can be used in the practice of this invention. Organic chloro compounds which are of particular interest are those in which the replaceable chlorine atoms are on carbon atoms attached to oxygen, sulfur or nitrogen by a single-bond as in ethers, thioethers and imides because of the excellent insecticidal properties of the products. Preferred organic chloro compounds are the chlorodioxanes and particularly the dichloro-p-dioxanes such as 2,3-dichloro-p-dioxane and 2,5-dichloro-p-dioxane; tetrachloro-p-dioxane; alpha-chloro-m-dioxane; the chlorodithianes such as 2,3-dichloro-p-dithiane; the chlorothioxanes such as 2,3-dichloro-p-thioxane; 4,5-dichloro-m-dioxolane; and the N(1-chloro-2-haloethyl) phthalimides, and particularly N(1,2-chloroethyl) phthalimide.

As stated, the process of this invention is carried out in the presence of a catalytic amount of a metal chloride catalyst. The catalysts which are used in the present process accelerate rather than initiate the reaction and are chlorides of zinc, iron and tin. Zinc and tin chlorides are preferred because they give the lightest colored products. While the catalysts are referred to as chlorides, it is to be understood that metals or salts which under the reaction conditions are converted into the metal chlorides may be used as equivalents because of the nature of the reaction, and it is not intended that the process should be limited to one in which the metal chloride is added as such to the reaction mixture. The amount of catalyst used in the process of the present invention is not critical. A catalytic amount will generally be in the range of about 0.05 to 2 mole percent based on the dithiophosphoric acid reactant, with about 0.5 to about 1.0 mole percent being preferred.

The reaction temperature is any temperature in the range of about 40° to about 200° C. at which reaction takes place but below the decomposition temperature of the product or any intermediate produced in the process. The particular temperature used will thus depend on the reactants used. Some intermediates such as the monochlorodioxanethiol-S-O,O-dialkyl phosphorodithioate produced from dichloro-p-dioxane and O,O-dialkyl dithiophosphoric acid, for instance, are unstable at temperatures above about 110° C. and require temperatures lower than might otherwise be required. Likewise, some products are unstable at elevated temperatures, and for this reason call for a preferred upper temperature limit of about 110° C. Generally, a temperature range between about 70° C. and about 95° C. for 4 to 6 hours will be sufficient to optimize yield and product purity.

The reaction is preferably carried out in a solvent which is inert in the reaction, although solvents are not necessary. When a solvent is used, aromatic volatile hydrocarbons such as benzene, toluene, xylenes, chlorobenzene, or cymene, cycloaliphatic volatile hydrocarbon such as cyclopentane or cyclohexane, or carbon tetrachloride are preferred because they have the desired dissolving power for the reaction mixture without high dissolving power for the hydrogen chloride produced and are readily removed after the reaction is complete by distillation. Although water is generally deleterious to substitution reactions of this type, trace amounts of water do not need to be excluded and completely anhydrous catalyst are not necessary unless the chloro organic compound is exceptionally reactive with water, as in the case of acid chlorides.

The improved process described by this invention, as stated, concerns carrying out the metal chloride catalyzed reaction defined by the equation

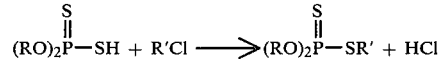

(where R and R' are as indicated above) under sufficient pressure to maintain the hydrogen chloride which is liberated by the reaction in the system during the course of the reaction. Usually, a pressure of at least about 5 psig will be adequate to realize the advantages of this invention. Preferably, however, the pressure will range from about 10 to about 100 psig, to optimize the yield and reaction rate and maximize product purity. The exact mechanisms by which the metal chloride catalyst and the hydrogen chloride interact under pressure to influence the rate of the reaction and the yield of product are not completely understood. One explanation might be that the maintenance of hydrogen chloride in the reaction system minimizes side reactions such as dehydrochlorination of the organic chloride reactant. Nonetheless, it has been found that similar advantages are not realized when the catalyzed reaction is carried out under conditions whereby the hydrogen chloride is removed or sequestered as it is formed, or when the catalyzed reaction is carried out under pressure in the presence of a sequestering agent.

Recovery of the dithiophosphoric acid ester products produced in accordance with the improved process of this invention is conventional and does not require special techniques. Usually the organic phase is washed with water or preferably water containing sufficient alkali to produce water-soluble salts of excess reactants, and solvent, if present, is removed by distillation. Further purification by selective solvent extraction or by adsorptive agents is not usually necessary and the product is a highly satisfactory insecticide without subsequent treatments.

The products of this invention can be used as the sole toxic agent in insecticidal formulations or, if desired, in admixture with other toxicants for modification of the properties of the individual toxicants.

What I claim and desire to protect by Letters Patent is:

1. In the process defined by the reaction:

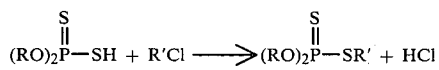

where R is an alkyl group having 1 to 4 carbon atoms and R'Cl is an organic chloride which contains at least one acid-replaceable chlorine atom on a carbon atom attached to oxygen, sulfur or nitrogen by a single bond, which reaction is effected in the presence of a catalytic amount of zinc chloride, ferrous chloride or stannous chloride and in the absence of a sequestering agent for the hydrogen chloride liberated by the reaction, the improvement which comprises conducting said reaction under sufficient pressure to maintain the liberated hydrogen chloride in the system during the course of the reaction.

2. The process of claim 1 wherein the reaction is conducted in an inert organic solvent.

3. The process of claim 2 in which the organic chloride is a chlorodioxane.

4. The process of claim 3 in which the chlorodioxane is a dichloro-p-dioxane.

5. The process of claim 4 in which the dichloro-p-dioxane is 2,3-dichloro-p-dioxane.

6. The process of claim 2 in which the organic chloride is N(1,2-dichloroethyl)phthalimide.

* * * * *